United States Patent

Pilato et al.

Patent Number: 5,883,112
Date of Patent: Mar. 16, 1999

[54] SYNERGISTIC COMPOSITIONS COMPRISING PESTICIDAL 5-AMINO-4-ETHYLSULFINYL-1-ARYLPYRAZOLES AND PIPERONYL BUTOXIDE

[75] Inventors: Michael Thomas Pilato, Cary; Charles Lee Haas, Garner, both of N.C.

[73] Assignee: Rhone-Poulenc Inc., Research Triangle Park, N.C.

[21] Appl. No.: 109,409

[22] Filed: Jul. 2, 1998

Related U.S. Application Data

[62] Division of Ser. No. 768,120, Dec. 17, 1996, Pat. No. 5,814,652.

[60] Provisional application No. 60/008,913, Dec. 20, 1995.

[51] Int. Cl.$^6$ .................. A01N 43/56; C07D 231/44
[52] U.S. Cl. .............. 514/404; 514/407; 548/367.4; 548/367.7; 548/371.1
[58] Field of Search .................. 514/404, 407; 548/367.4, 367.7, 371.1

[56] References Cited

U.S. PATENT DOCUMENTS

| | | | |
|---|---|---|---|
| 2,485,681 | 10/1949 | Wachs, I | 514/464 X |
| 2,550,737 | 1/1951 | Wachs, II | 514/464 |
| 4,685,957 | 8/1987 | Gehring et al. | 71/92 |
| 4,740,232 | 4/1988 | Gehring et al. | 71/92 |
| 4,772,312 | 9/1988 | Schallner et al. | 71/92 |
| 4,804,675 | 2/1989 | Jensen-Korte et al. | 514/407 |
| 4,822,810 | 4/1989 | Lindig et al. | 514/407 |
| 4,863,937 | 9/1989 | Gehring et al. | 514/333 |
| 5,232,940 | 8/1993 | Hatton et al. | 514/407 |
| 5,637,607 | 6/1997 | Pilato et al. | 514/404 |

FOREIGN PATENT DOCUMENTS

| | | |
|---|---|---|
| 0234119 | 9/1987 | European Pat. Off. |
| 0295117 | 12/1988 | European Pat. Off. |
| 0295118 | 12/1988 | European Pat. Off. |
| 0350311 | 1/1990 | European Pat. Off. |
| 0398499 | 11/1990 | European Pat. Off. |
| 0511845 | 11/1992 | European Pat. Off. |
| 2136427 | 9/1984 | United Kingdom. |
| 87/03781 | 7/1987 | WIPO. |
| 93/06089 | 4/1993 | WIPO. |
| 94/21606 | 9/1994 | WIPO. |
| 96/23411 | 8/1996 | WIPO. |

OTHER PUBLICATIONS

Merck, The Merck Index, Eighth Edition, p. 839, 1968.

*Primary Examiner*—Floyd D. Higel
*Attorney, Agent, or Firm*—Burns, Doane, Swecker & Mathis, L.L.P.

[57] ABSTRACT

The invention relates to a synergistic pesticidal composition comprising:

(a) a pesticidally effective amount of a compound having the formula:

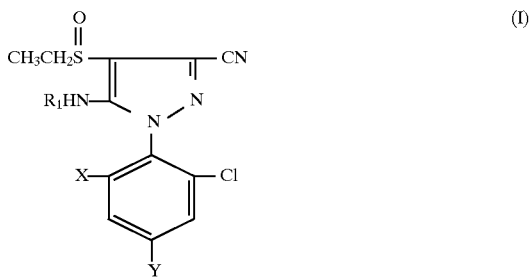

(I)

wherein X is chlorine or bromine, Y is trifluoromethyl or trifluoromethoxy and $R_1$ is hydrogen, methyl or ethyl; and (b) a synergistic amount of piperonyl butoxide.

29 Claims, No Drawings

SYNERGISTIC COMPOSITIONS COMPRISING PESTICIDAL 5-AMINO-4-ETHYLSULFINYL-1-ARYLPYRAZOLES AND PIPERONYL BUTOXIDE

CROSS-REFERENCE TO RELATED APPLICATION

This application is a divisional of U.S. application Ser. No. 08/768,120, filed Dec. 17, 1996, now U.S. Pat. No. 5,814,652, which claims the priority of U.S. Provisional Patent Application Ser. No. 60/008,913, filed Dec. 20, 1995, both earlier applications being incorporated by reference herein in their entireties and relied upon.

BACKGROUND OF THE INVENTION

1. Field of the Invention

This invention relates to novel 5-amino-4-ethylsulfinyl-1-arylpyrazole compounds, compositions containing them, processes for their preparation and their use as insecticides.

2. Description of the Related Art

5-Amino-4-ethylsulfur containing pyrazoles are known in the literature. European Patent Publication No. 0295117 discloses 5-amino-3-cyano-1-(2,6-dichloro-4-trifluoromethylphenyl)-4-ethylsulfonylpyrazole and 5-amino-3-cyano-1-(2,6-dichloro-4-trifluoromethylphenyl)-4-ethanesulfonylpyrazole (compounds 70 and 81 respectively), which are described as having generally good pesticidal properties and in particular as effective against *Plutella xylostella* (diamondback moth) in a contact spray test. However, systemic action by insecticides is a much less frequent property than such a typical contact action. The term "systemic" describes a chemical that is absorbed by a plant through foliar spray, seed treatment, seed soak, soil application by means of granular side dressing, granular in-furrow or in-furrow spray, and transported throughout the plant system. It is highly advantageous to have a compound which can be applied to the under- and the above-ground portions of a plant and possesses systemic activity such as to render the plant toxic to pests. The importance of the systemic insecticidal activity is that it can provide insect control where direct contact in practice is inefficient or very difficult for control of sucking insects that frequently attack other portions of the plant that are not easily accessible, such as downside or underside of leaves. The insects of this type, for examples, are aphids and plant bugs, stinkbugs, found on cotton, cereals, vegetables, fruit trees. While European Patent Publication No. 0295117 discloses, in general terms, the possibility of N-phenylpyrazoles having systemic properties, no examples of such properties are given. PCT published application WO87/03781 also discloses pesticidally active N-phenylpyrazoles but also fails to specifically disclose systemic utility.

It is therefore an object of the invention to provide new compounds having systemic insecticidal properties.

It is a further object of this invention to provide new compounds having a good level of safety towards mammals and aquatic organisms.

It is a further object of the invention to provide compounds having useful properties against pests found in non-agricultural areas.

These and other objects of the invention will become apparent from the description that follows and can be achieved in whole or in part by the present invention.

SUMMARY OF THE INVENTION

The present invention provides 5-amino-4-ethylsulfinylpyrazoles of formula (I):

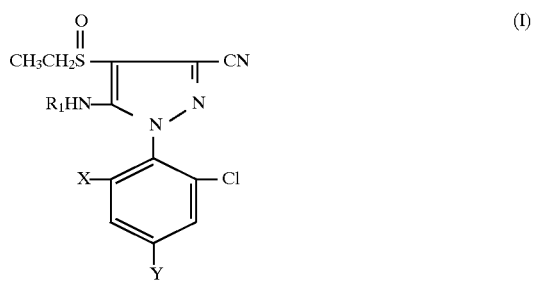

wherein X is chlorine or bromine; Y is trifluoromethyl or trifluoromethoxy and $R_1$ is hydrogen, methyl or ethyl.

Surprisingly, it has been found that these compounds provide highly beneficial and advantageous systemic activity against insect pests. Furthermore, the compounds exhibit a high degree of safety towards mammals and aquatic organisms.

Synergistic compositions comprising a compound of formula (I) and piperonyl butoxide are described hereinafter.

DETAILED DESCRIPTION OF THE INVENTION

Preferred compounds of formula (I) above are those in which X is chlorine and Y is trifluoromethyl.

Compounds of formula (I) above in which $R_1$ is hydrogen or methyl are also preferred.

Particularly preferred compounds of formula (I) include the following:

1. 5-amino-3-cyano-1-(2,6-dichloro-4-trifluoromethylphenyl)-4-ethylsulfinylpyrazole;
2. 5-amino-3-cyano-1-(2,6-dichloro4-trifluoromethoxyphenyl)-4-ethylsulfinylpyrazole;
3. 5-amino-1-(2-bromo-6-chloro-4-trifluoromethylphenyl)-4-ethylsulfinylpyrazole;
4. 5-amino-1-(2-bromo-6-chloro4trifluoromethoxyphenyl)4-ethylsulfinylpyrazole;
5. 3-cyano-1-(2,6-dichloro-4-trifluoromethylphenyl)4-ethylsulfinyl-5-methylaminopyrazole;
6. 3-cyano-1-(2,6-dichloro-4-trifluoromethylphenyl)4-ethylsulfinyl-5-ethylaminopyrazole; and
7. 1-(2-bromo-6-chloro4-trifluoromethoxyphenyl)4-ethylsulfinyl-5-ethylaminopyrazole.

The numbers 1 to 7 are assigned to these compounds for reference and identification hereafter.

Of these compounds, compound numbers 1 and 5 are most preferred.

METHODS OR PROCESSES FOR PREPARATION

The compounds of formula (I) above may be prepared by the application or adaptation of known methods, i.e. methods heretofore used or described in the literature, for example as described below.

According to a feature of the present invention, compounds of formula (I) above, in which $R_1$ is hydrogen, may be prepared by the reaction of a hydrazine of formula (II) or an acid addition salt thereof:

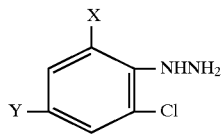

wherein X and Y are as defined above, with a compound of formula (III):

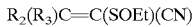

wherein $R_2$ is cyano and $R_3$ is chlorine or fluorine (preferably chlorine).

The reaction is generally performed in an inert solvent, preferably ether or tetrahydrofuran and optionally in the presence of a base (e.g. triethylamine or sodium acetate), and at a temperature from 0° C. to the reflux temperature of the solvent. When an acid addition salt of the hydrazine is used (preferably the hydrochloride), the reaction is generally effected in the presence of a base such as an alkali metal salt (e.g. sodium or potassium acetate, carbonate or bicarbonate).

According to a further feature of the present invention, compounds of formula (I) above may also be prepared by oxidizing a compound of formula (IV):

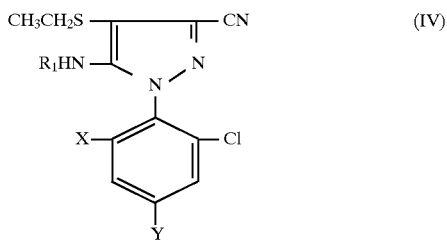

wherein $R_1$, X and Y are as defined above, using an oxidizing agent. The reaction is generally performed in a solvent (e.g. trifluoroacetic acid, dichloromethane or methanol) using an oxidizing reagent such as hydrogen peroxide or metachloroperbenzoic acid at a temperature between −30° C. and the boiling temperature of the solvent. More preferable conditions utilize hydrogen peroxide in methanol.

According to a further feature of the present invention, compounds of formula (I) above in which $R_1$ is hydrogen may also be prepared by the reaction of a compound of formula (V):

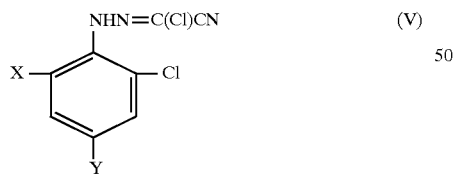

wherein X and Y are as defined above, with a compound of formula (VI):

Preferably, the molar ratio of reactants is about 1:1. The reaction is generally performed in the presence of an anhydrous inert organic solvent (e.g. ethanol) and a molar equivalent of a base (e.g. sodium ethoxide) at a temperature from 0° to 50° C.

According to a further feature of the present invention, compounds of formula (I) above may also be prepared by the reaction of a compound of formula (VII):

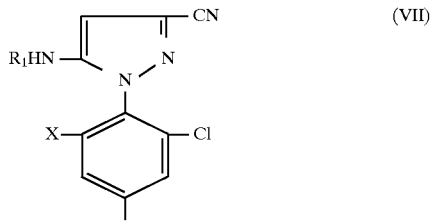

wherein X, Y and $R_1$ are as defined above, with a compound of formula $EtS(O)Z_1$, wherein $Z_1$ is a leaving group. Suitable leaving groups include halogen, alkylthio, arylthio, alkylsulfinyl, alkylsulfonyl, arylsulfinyl, arylsulfonyl, sulfate, tosylate, azido, nitro, alkoxy or aryloxy, preferably halogen, especially bromine, chlorine, iodine or fluorine.

According to a further feature of the present invention, compounds of formula (I) above in which $R_1$ is methyl or ethyl may also be prepared by the reaction of the corresponding compound of formula (I) above in which $R_1$ is hydrogen with a methylating or ethylating agent in the presence of a base. Preferred methylating agents include methyl halides, e.g. iodomethane, bromomethane and chloromethane; preferred ethylating agents include ethyl iodide. The reaction may be conducted in a variety of media including aprotic and protic solvents. Examples of aprotic solvents are tetrahydrofuran (THF), dimethylformamide (DMF), toluene and ether; examples of protic solvents include water and alcohols (such as ethanol and isopropyl alcohol). The reaction is usually performed at a temperature of from about −20° C. to about 250° C., preferably from about −5° C. to about 150° C. Suitable bases include hydrides (e.g. sodium or potassium hydride), a carbonate (e.g. potassium carbonate) and organic base (e.g. triethylamine or a guanidine, such as tetramethyl guanadine), an amide (e.g. sodium or potassium amide) or an alkoxide (e.g. sodium methoxide or potassium methoxide).

According to a further feature of the present invention, compounds of formula (I) above in which $R_1$ is methyl or ethyl may also be prepared by reacting the corresponding compound of formula (I) in which $R_1$ is hydrogen with an orthoformate of formula $CH(OR_{12})_3$ or $MeC(OR_{12})_3$, wherein $R_{12}$ is alkyl (generally of 1 to 4 carbon atoms), to give a compound of formula (VIII):

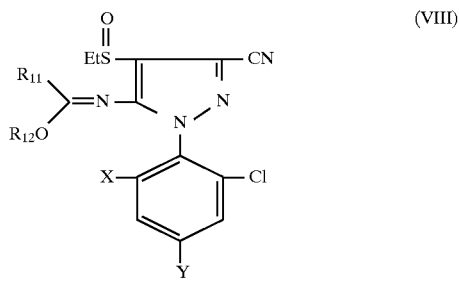

wherein $R_{12}$, X and Y are as defined above and $R_{11}$ is hydrogen or methyl, which is subsequently treated with a reducing agent. The reaction with the orthoformate of formula $CH(OR_{12})_3$ or $MeC(OR_{12})_3$ is preferably conducted in the presence of an acid catalyst such as hydrochloric acid, p-toluenesulfonic acid, a Lewis acid (e.g. aluminum chloride, boron trichloride, boron trifluoride or zinc chloride). The reaction can be conducted optionally in a media of various polarity and solvating power. Typically the reaction is performed at from about −20° C. to about 350° C., preferably from about 50° C. to about 200° C. The reaction can be facilitated with azeotropic removal of the alcohol formed as a by-product during the reaction. Compounds of formula (VIII) above are novel and as such constitute a further feature of the present invention.

According to a further feature of the present invention, compounds of formula (I) may also be prepared by the reaction of a compound of formula (IX):

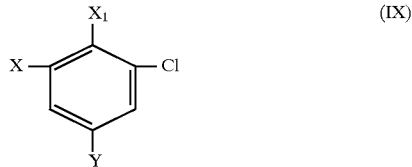

wherein X and Y are as defined above, and $X_1$ is halogen, with a compound of formula (X):

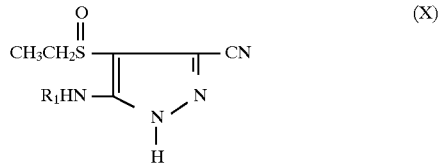

wherein $R_1$ is as defined above. The coupling reaction may be carried out in an inert solvent that can solvolyze both reactants for coupling, and may be organic, inorganic or a mixture of both. Suitable solvents include DMF, THF, methanol, and water. The reaction may be catalyzed using a base catalyst, such as a metal carbonate, a metal hydroxide, an organic base such as an amine or a guanidine or a hydride such as sodium hydride. The reaction may be carried out at a temperature of from about −20° C. to about 250° C.

Compounds of formulae (II), (III), (IV), (V), (VI), (VII), (IX) and (X) are known or may be prepared by the application or adaptation of known methods.

The following non-limiting Examples and Reference Examples illustrate the preparation of compounds of the invention and the intermediates in their preparation.

EXAMPLE 1

To a solution of 5-amino-3-cyano-1-(2,6-dichloro4-trifluoromethylphenyl)-4-ethylthiopyrazole (22.25 g, 0.058 mol.) in methanol was added a solution of sulfuric acid (1.5 g) in isopropanol. Hydrogen peroxide (6.95 g, 0.2 mol., 30% aqueous solution) was added and the temperature raised to 60° C. After two hours, the reaction was filtered and the collected solids were washed with methanol. The filtrate was added to water and stirred for 30 minutes. The solid was collected and air-dried. All combined solids were recrystallized from methanol to leave the title compound (18.4 g), melting point about 174° C.

By proceeding in a similar manner, the following compounds were prepared:
5-amino-3-cyano-1-(2,6-dichloro-4-trifluoromethoxyphenyl)-4-ethylsulfinylpyrazole (Compound 2), m.p. 178° C.;
5-amino-1-(2-bromo-6-chloro-4-trifluoromethylphenyl)4-ethylsulfinylpyrazole (Compound 3), m.p. 157° C.;
5-amino-1-(2-bromo-6-chloro-4-trifluoromethoxyphenyl)-4-ethylsulfinylpyrazole (Compound 4), m.p. 173° C.

EXAMPLE 2

Preparation of 3-cyano-1-(2,6-dichloro-4-trifluoromethylphenyl)-4-ethylsulfinyl-5-methylaminopyrazole (Compound 5)

To a mixture of 5.3 g of 1-(2,6-dichloro-4-trifluoromethyl)phenyl-3-cyano-4-ethylsulfinyl-5-ethoxymethyleneiminopyrazole in acetic acid was added 1.47 g (23.4 mmol.) of sodium cyanoborohydride in four portions at room temperature during a period of 2 hr. The mixture was partitioned between water and dichloromethane. The organic layer was dried over anhydrous sodium sulfate and solvent evaporated. The residue was purified by a flash column chromatography on silica gel using 60% ethyl acetate in hexane to give 2.1 g of 3-cyano-1-(2,6-dichloro4-trifluoromethylphenyl)-4-ethylsulfinyl-5-methylaminopyrazole (as a white solid, melting point of 154°–155° C.).

Elemental analysis for the product indicated the following:

Analysis: $C_{14}H_{11}Cl_2F_3N_4O_1S_1$ Calculated: C, 40.89; H, 2.70; N, 13.62; Cl, 17.24; S, 7.80; Found: C, 40.52; H, 2.85; N, 12.97; Cl, 17.09; S, 7.97.

By proceeding in a similar manner, the following compounds were prepared:
3-cyano-1-(2,6-dichloro-4-trifluoromethyl)phenyl4-ethylsulfinyl-5-ethylaminopyrazole (Compound 6), m.p. 142° C.;
1-(2-bromo-6-chloro-4-trifluoromethoxy)phenyl-4-ethylsulfinyl-5-ethylaminopyrazole (Compound 7), m.p. 133° C.

Reference Example 1

Preparation of 1-(2,6-dichloro-4-trifluoromethyl) phenyl-3-cyano-4-ethylsulfinyl-5-ethoxymethyleneiminopyrazole To 5.0 g (12.7 mmol.) of 1-(2,6-dichloro-4-trifluoromethyl)phenyl-3-cyano-4-ethylsulfinyl-5-aminopyrazole (Compound 1) was added 100 ml of triethyl orthoformate, 20 ml of THF and 50 ml of toluene. The resultant mixture was heated on a steam bath. To the solution was added a catalytic amount of hydrochloric acid. The mixture was heated on a steam bath for 20 min., followed by evaporation of the mixture on rotavapor under reduced pressure at 70° C. A total of 300 ml of carbon tetrachloride was added in portions and the mixture was continuously evaporated on a rotary evaporator at 70° C. The evaporation continued until all ethanol formed was removed and excess triethyl orthoformate was removed to give a thick oil. The oil was analyzed by $H_1$-NMR and shown to be pure 1-(2,6-dichloro-4-trifluoromethyl)phenyl-3-cyano-4-ethylsulfinyl-5-ethoxymethyleneiminopyrazole, which was used without further purification.

According to a feature of the present invention these are provided compositions comprising a compound of formula (I) in association with, and preferably homogeneously dispersed in, a pesticidally, e.g. agriculturally acceptable diluent or carrier. In practice, the compounds of the invention most frequently form part of compositions. These compositions can be employed to control pest, e.g. insect pests. The compositions may be of any type known in the art as suitable for application to the desired pest or habitat thereof. These compositions contain at least one compound of the invention, such as described earlier, as the active ingredient in combination or association with one or more other compatible components which are, for example, solid or liquid carriers or diluents, adjuvants, surface active-agents, or the like appropriate for the intended use and which are acceptable, e.g. agronomically acceptable.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, liquid sprays, dusts, granules, fogs, foams, emulsions or the like.

The effective use dose of the compounds employed in the invention can vary within wide limits, particularly depending on the nature of the pest to be eliminated or degree of infestation, for example, of crops with these pests. In general, the compositions (concentrated or diluted ready to use) according to the invention usually contain from about 0.001 to about 95% (by weight) of one or more active ingredients according to the invention, from about 1 to about 95% of one or more solid or liquid carriers and, optionally, from about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. As solid carriers for granules, the following are suitable: crushed or fractionated natural rocks such as calcite, marble, pumice, sepiolite and dolomite; synthetic granules of inorganic or organic meals, granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutyl ketone, or isophorone; petroleum fractions such as paraffinic or aromatic hydrocarbons, particularly xylenes or alkyl naphthalenes; mineral or vegetable oils; aliphatic chlorinated hydrocarbons, particularly chlorobenzenes; water-soluble or strongly polar solvents such as dimethylformamide, dimethylsulfoxide, or N-methylpyrrolidones; N-allylpyrrolidones; trialkyl phosphates; liquefied gases; or the like; or a mixture thereof.

The surface-active agent may be an emulsifying agent, dispersing agent or wetting agent of the ionic or non-ionic type or a mixture of such surface-active agents. Among these are e.g., salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as polymer dispersants, stabilizers or colorants. Adhesives such as carboxymethylcellulose or natural or synthetic polymers in the form of powders, granules or latices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc. The polymers can be random or block copolymers of alkyl polyethylene glycols. The physical shapes of the polymer surfactants can be linear or comb types. The comb polymers are generally either polyacrylates or polymethacrylates grafted with polyethylene glycol or ethoxylated phenolic polymers. Other polymeric surfactants include alkyl polysaccharides, alkyl polyglycosides, fatty acid sucroglycerides, copolymers of vinyl pyrrolidone-vinyl acetates, vinylpyrrolidone-ethylmethacrylate, methyl vinyl ether-maleic anhydride, and alkylated vinylpyrrolidone polymers.

Compositions containing compounds of general formula (I) which may be applied to control insect pests, may also contain synergists (e.g. piperonyl butoxide or sesamex), stabilizing substances, other insecticides, acaricides, plant nematicides, fungicides, e.g. benomyl and iprodione, bactericides, arthropod attractants or repellents or pheromones, deodorants, flavoring agents, dyes, or auxiliary therapeutic agents, e.g. trace elements. These may be designed to improve potency, persistence, safety, uptake where desired or spectrum of pests controlled or to enable the composition to perform other useful functions in the same animal or area treated.

In particular, it has unexpectedly been found that the combination of a compound of general formula (I) with piperonyl butoxide, against a number of important pest species such as *Aphis gossypi* and *Myzus persicae*, results in a remarkably improved level of pesticidal activity and speed of action and thus constitutes a further feature of the present invention.

Preferably the piperonyl butoxide is used in combination with the compound of general formula (I) at rates of from about 10 to about 200 g/ha, more preferably from about 20 to about 100 g/ha, even more preferably about 40 g/ha.

Examples of other pesticidally active compounds which may be included in, or used in conjunction with, the compositions of the present invention are: acephate, chlopyrifos, demeton-S-methyl, disulfoton, ethoprofos, fenitrothion, fenamiphos, fonofos, iprodione, isazophos, isofenphos, malathion, monocrotophos, parathion, phorate, phosalone, pirimiphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

Formulations which are suitable in these mixtures are those normally used for oral administration of insecticides to animals, such as solid or liquid formulations. Solid formulations may be made by mixing these mixtures with all kinds of animal food, preferably with flavoring agents. Liquid formulations can be made as suspensions in natural oil, preferably with additives acceptable in animal health such as flavoring agents, sweeteners, anti-bitterness agents.

For their agricultural application, the compounds of the formula (I) are therefore generally in the form of compositions, which are in various solid or liquid forms.

Solid forms of compositions which can be used are dusting powders (with a content of the compound of formula (I) ranging up to 80%), wettable powders or granules (including water-dispersible granules), particularly those obtained by extrusion, compacting, impregnation of a granular carrier, granulation starting from a powder (the content of the compound of formula (I) in these wettable powders or granules being between about 0.5 and about 95%). Solid homogeneous or heterogeneous compositions containing one or more compounds of general formula (I) for example granules, pellets, briquettes or capsules, may be used to treat standing or running water over a period of time. A similar effect may be achieved using trickle or intermittent feeds of water-dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powders for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates, most frequently comprise from about 5 to about 90% by weight of the active ingredient, while the emulsions or solutions which are ready for application contain, in their case, from about 0.01 to about 20% of the active ingredient. Besides the solvent, the emulsifiable or soluble concentrates may contain, when required, from about 2 to about 50% of suitable additives, such as stabilizers, surface-active agents, penetrating agents, corrosion inhibitors, colorants or adhesives. Emulsions or microemulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

All these aqueous dispersions, emulsions, microemulsions or spraying mixtures can be applied, for example, to crops by any suitable means, chiefly by spraying, at rates which are generally of the order of from about 100 to about 1,200 liters of spraying mixture per hectare, but may be higher or lower (e.g. low or ultra-low volume) depending upon the need or application technique. The compounds or compositions according to the invention are conveniently applied to vegetation and in particular to roots, seeds, stems or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (such as by fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The use of emulsifiable concentrate formulations is particularly preferred where the compounds of the invention are used for foliar sprays in crops such as vegetables and cotton; or for soil in-furrow sprays.

The wettable powders (or powders for spraying) are usually prepared so that they contain from about 10 to about 95% by weight of active ingredient, from about 20 to about 90% of a solid carrier, from about 0 to about 5% of a wetting agent, from about 3 to about 10% of a dispersing agent and, when necessary, from about 0 to about 10% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. These powders may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with inert filler and a little water, e.g. from about 1 to about 20% by weight, or with an aqueous solution of a dispersing agent or binder, followed by drying and screening), or by a dry route (compacting followed by grinding and screening).

The use of the compositions of the invention in the form of granules is particularly preferred for soil applications, where the systemic properties of the compounds is especially useful.

Specific Composition Examples

The following composition EXAMPLES made by well-known techniques or those described herein, illustrate compositions for use against insects and other pests. These compositions comprise, as active ingredient, one or more compounds of general formula (1), such as those described above. A composition as described in these EXAMPLES can be diluted in water to give a sprayable composition at concentrations suitable for use in the field. Generic chemical descriptions of the trade names (for which all of the following percentages are in weight percent), used in the composition EXAMPLES 3A–3I exemplified below, are as follows:

| Trade Name | Chemical Description |
|---|---|
| Igepal CO630 | Nonyl phenol ethoxylate |
| Rhodacal 70/B | Calcium dodecylbenzene sulfonate |
| Geronol | Mixtures of calcium dodecylbenzene sulfonate and alkylphenol ethoxylate |
| Agrosorb 24/28 | Bentonite |
| Morwet D-425 | Na alkylated naphthalene sulfonate |
| Rhodorsil | Polydimethylsiloxane |
| Proxel GXL | 1,2-benzisothiazolin-3-one |
| Rubine Toner 2BO | Red pigment. |
| Biodac | Cellulose complex |
| Soprophor 860/P | Branched chain isodecyl alcohol ethoxylate (non-ionic) |
| Soprophor FLK | Tristyrylphenol ethoxylate, potassium salt |

EXAMPLE 3A

The following emulsifiable concentrate (EC) formulation was prepared:

| | |
|---|---|
| Compound 1: | 10% |
| N-Octyl pyrrolidone | 36% |
| Butyrolactone | 24% |
| Igepal CO630 | 24% |
| Rhodacal 70/B | 6% |

Similar EC formulations may be prepared by replacing the pyrazole (Compound 1) with other compounds of formula (I).

EXAMPLE 3B

A granular formulation was prepared containing the following:

| | |
|---|---|
| Compound 1 | 1.5% |
| N-Methyl pyrrolidone | 10.5% |
| Geronol S/245 | 1.5% |
| Geronol S/256 | 1.5% |
| Propylene glycol | 5% |
| Agrosorb 24/48 | 80.0% |

Similar granular formulations may be prepared by replacing the pyrazole (Compound 1) with other compounds of formula (I).

EXAMPLE 3C

A seed dressing formulation was prepared containing the following ingredients:

| | |
|---|---|
| Compound 1 | 44.26% |
| Soprophor 860/P | 0.82% |
| Soprophor FLK | 2.05% |
| Morwet D-425 | 2.05% |
| Rhodorsil 454 | 0.08% |
| Rhodorsil 432 | 0.66% |
| Rhodopol 23 | 0.2% |
| Propylene glycol | 4.10% |
| Proxel GXL | 0.1% |
| Rubine Toner 2BO | 0.82% |
| Water | 44.86% |

Similar seed treatment formulations may be prepared by replacing the pyrazole (Compound 1) with other compounds of formula (I).

EXAMPLE 3D

A wettable dispersible granule (WDG) is prepared containing the following ingredients:

| | |
|---|---|
| Compound 1 | 80% |
| Sodium oleyl methyl taurate | 3% |
| Sodium polyacrylate | 2.7% |
| Sodium lignosulfonate | 14% |
| Methyl polysiloxane | 0.3% |

Similar WDGs may be prepared by replacing the pyrazole (Compound 1) with other compounds of formula (I).

EXAMPLE 3E

An emulsifiable concentrate formulation (EC) is prepared containing the following ingredients:

| | |
|---|---|
| Compound 1 | 0.06% |
| Alkyl polyethoxyether phosphates | 12% |
| Triethyl phosphate | 12% |
| Aromatic 150 | 75.94% |

Similar ECs may be prepared by replacing the pyrazole (Compound 1) with other compounds of formula (I).

EXAMPLE 3F

A suspension concentrate formulation is prepared containing the following ingredients:

| | |
|---|---|
| Compound 1 | 20% |
| Methyl caprylate caprate | 30% |
| Propylene glycol | 5% |
| Nonyl phenol ethoxylate (HLB = 9) | 2% |
| Sodium lignosulfonate | 2% |
| Methyl polysiloxane | 0.4% |
| Water | 40.6% |

Similar suspension concentrates may be prepared by replacing the pyrazole (Compound 1) with other compounds of formula (I).

EXAMPLE 3G

A solution concentrate formulation is prepared containing the following ingredients:

| | |
|---|---|
| Compound 1 | 15% |
| N-Methyl pyrrolidone | 50% |
| Tristyrylphenol ethoxylate (HLB = 12.5) | 15% |
| Methyl coconate | 20% |

Similar solution concentrates may be prepared by replacing the pyrazole (Compound 1) with other compounds of formula (I).

EXAMPLE 3H

A fertilizer granule is coated with the compound of the invention to provide a composition having the following ingredients:

| | |
|---|---|
| Compound 1 | 0.03% |
| N-Methyl pyrrolidone | 0.10% |
| Nonylphenol ethoxylate (HLB = 8) | 0.3% |
| Calcium dodecyl benzene sulfonate | 0.1% |

-continued

| | | |
|---|---|---|
| N-P-K Fertilizer granule (20/40 mesh) 20-12-16 | | 99.47% |

Similar fertilizer granules may be prepared by replacing the pyrazole (Compound 1) with other compounds of formula (I).

EXAMPLE 31

A granule of BIODAC is produced by coating with the compound of the invention to provide a composition having the following ingredients:

| | |
|---|---|
| Compound 1 | 0.03% |
| N-Methyl pyrrolidone | 0.10% |
| Nonylphenol ethoxylate (HLB = 8) | 0.3% |
| Calcium dodecyl benzene sulfonate | 0.1% |
| Propylene glycol | 2.0% |
| BIODAC granules (30/60) | 97.47% |

Similar granules may be prepared by replacing the pyrazole (Compound 1) with other compounds of formula (I).

As is evident from the foregoing pesticidal uses, the present invention unexpectedly provides systemic insecticidal compounds, systemic insecticidal compositions, and systemic insecticidal methods of use of said compounds for the control of a number of insect pest species, which especially includes aphids, hoppers, and various bugs.

A feature of the present invention therefore provides a method of control of pests, e.g. insect pests at a locus which comprises the treatment of the locus (e.g., by application or administration) with an effective amount of a compound of general formula (I). The locus may be an area used, or to be used, for growing a crop. The locus is, for example, a plant part and includes, for example, the plant's seeds or the plant's roots. Alternatively, the locus is the medium in which the plants grow, e.g., soil or water.

These compounds are especially useful in the control, via systemic action, of foliar insect pests, which feed on the above-ground portions of plants. Control of foliar pests is thus provided by application to the plant roots or plant seeds, with subsequent systemic translocation to the above-ground portions of the plants. It will be understood that the term "insects" is used in this specification in its colloquial sense as including arthropod pests.

As indicated above, the compounds of the invention are advantageously used to systemically control insect pests. The term control is meant to include, for example, killing, inhibiting, combating, suppressing, repelling or deterring the insect pest or alternatively, by these means or others, protecting a plant in order to prevent damage to the plant caused by the insect pest.

The invention, as previously described, provides methods of control of insect pests via application or administration of an effective amount of at least one compound of formula (I) at a locus which comprises treatment of the locus. The classes of insect pests which may be systemically controlled by a compound of the invention include the Homoptera order (piercing-sucking), Hemiptera order (piercing-sucking), and Thysaroptera order. The invention is especially appropriate for aphids and thrips.

In practical use for the control of insect pests, a method, for example, comprises applying to plants or parts thereof, or to the medium in which they grow, an effective amount of a compound of the invention. More specifically, for such a method, the active compound is generally applied to the plant roots, the plant seeds or the soil or water in which the plants grow, at an effective amount of the compound or composition containing said compound sufficient to control a foliar pest infestation.

As described herein, the compounds and their compositions can be applied in effective amounts by a number of different techniques readily known to one skilled in the art. These include, for example: as a soil application to field crops from about 5 to about 1000 g a.i./ha, preferably from about 50 to about 250 g a.i./ha; as a root dip to seedlings or drip irrigation to plants as a liquid solution or suspension containing from about 0.075 to about 1000 mg a.i./l, preferably from about 25 to about 200 mg a.i./l; and as a seed treatment of from about 0.03 to about 40 g a.i./kg of seed, preferably from about 0.5 to about 7.5 g a.i./kg of seed. These rates may be higher or lower than the specified ranges depending on factors such as type and size of seed and pest to be controlled. Under ideal conditions, depending on the pest to be controlled, the lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. The actual compositions employed and their effective rate of application will be selected to achieve the desired effect(s) by the user or other person skilled in the art.

For soil application, the active compound, generally in a formulated composition, is distributed evenly over the area to be treated (i.e., for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place or after sprouting.

Additionally, a method of control may also comprise treatment of the seed prior to planting with subsequent control of foliar insects attacking the aerial parts of the plants effected after planting the seed. The methods of control of pests by the invention compounds thus provide control of pests which feed on parts of the plant remote from the point of application, e.g., leaf-feeding insects which are controlled via systemic action of the active compound when applied, for example, to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, ornamentals, or plantation or forest trees, or turf, for example: cereals (such as oats, barley, wheat or rice); vegetables (such as beans, cole crops, curcurbits, lettuce, spinach, celery, onions, tomatoes or asparagus); field crops (such as cotton, tobacco, maize, sorghum, hops, peanuts or soybeans); small fruits (such as cranberries or strawberries); plantations (such as coffee or cocoa); orchards or groves (such as of stone (peaches, almonds or nectarines), pomes (apples) or pit fruit, citrus (oranges, lemons, grapefruit), pecan or avocado trees; grape vineyards; ornamental plants; flowers or vegetables or shrubs under glass or in gardens or parks; forest trees (both deciduous and evergreen) in forests, plantations or nurseries; or turf.

EXAMPLE A1

The following representative test procedures, using the compounds of the invention, were conducted to determine the pesticidal use and activity of compounds of the invention. The specific species tested were as follows:

| GENUS, SPECIES | COMMON NAME | ABBREVIATION |
|---|---|---|
| Schizaphis graminum | Greenbug aphid | TOXOGR |
| Aphis gossypii | Cotton aphid | APHIGO |

The test compounds were formulated for use according to the following methods used for each of the test procedures.

Test Procedures

A stock solution or suspension was prepared by adding 15 mg of the test compound to 250 mg of dimethylformamide, 1250 mg of acetone and 3 mg of the emulsifier blend referenced above. Water was then added to provide a test compound concentration of 150 ppm. When necessary, sonication was provided to ensure complete dispersion.

The above formulated test compounds were then evaluated for their pesticidal activity at the specified concentrations, in ppm (parts per million) by weight, according to the following test procedure:

Cotton aphid (on cotton) and greenbug (on sorghum)—systemic evaluation: A stock solution or suspension was prepared to deliver 5 ml of a 20 ppm soil concentration dose (and subsequent dilutions of 10.0, 5.0, 2.5, 1.25 and 0.625 ppm) as a drench to 6 cm pots containing cotton and sorghum plants. The cotton plants were previously infested with cotton aphids about two days before treatment and greenbug one day before treatment. After holding the plants about three days, the plants were rated for aphid activity. Again at six days, the plants were rated for aphid activity and the cotton aphids and greenbugs were counted and mortality was assessed. Mortality was assessed six days after infestation.

RESULTS

LC50 OF FOLIAR PESTS WITH A SOIL DRENCH APPLICATION OF COMPOUNDS (IN PPM, SOIL CONCENTRATION)

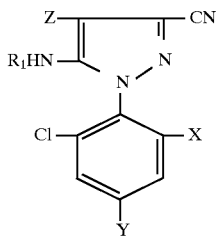

| CPD. NO. | X | Y | R$_1$ | Z | =APHIGO =COTTON | =TOXOGR =SORGHUM |
|---|---|---|---|---|---|---|
| 1 | Cl | CF$_3$ | H | SOEt | 0.21 | 0.6 |
| 2 | Cl | OCF$_3$ | H | SOEt | 0.9 | 0.2 |
| 3 | Br | CF$_3$ | H | SOEt | 0.8 | 1.0 |
| 4 | Br | OCF$_3$ | H | SOEt | ca2.0 | 1.0 |
| 5 | Cl | CF$_3$ | CH$_3$ | SOEt | 0.26 | 0.16 |
| 6 | Cl | CF3 | Et | SOEt | 3.5 | 1.1 |
| 7 | Br | OCF$_3$ | Et | SOEt | 13 | 1.2 |

-continued

| CPD. NO. | X | Y | R$_1$ | Z | =APHIGO =COTTON | =TOXOGR =SORGHUM |
|---|---|---|---|---|---|---|
| P1 | Cl | CF$_3$ | H | SEt | 3.85 | >20 |
| P2 | Cl | CF$_3$ | H | SO$_2$Et | 10 | 22 |
| P3 | Cl | CF$_3$ | H | SOCF$_3$ | 11.3 | >20 |

NOTE: APHIGO = cotton aphid; TOXOGR = greenbug
P1 is compound 70 of EP-A-0295117, 5-amino-3-cyano-1-(2,6-dichloro-4-trifluoromethylphenyl)-4-ethylsulfenylpyrazole.
P2 is compound 81 of EP-A-0295117, 5-amino-3-cyano-1-(2,6-dichloro-4-trifluoromethylphenyl)-4-ethanesulfonylpyrazole.
P3 is compound 52 of EP-A-0295117, 5-amino-3-cyano-1-(2,6-dichloro-4-trifluoromethylphenyl)-4-trifluoromethanesulfinylpyrazole, also known as fipronil.

EXAMPLE A2

The following example illustrates the biological interaction between the compounds of the invention and piperonyl butoxide.

Method

Compound 1, as an EC formulation, was formulated with water to the appropriate dilution to yield rates of 50, 12.5 and 3.13 g/ha. Additionally, piperonyl butoxide was included with the compound 1 dilutions at rates of 10, 20 or 40 g/ha as a tank mix. The tank mix solutions were applied using a track sprayer to deliver 200 l/ha spray volume at 40 p.s.i. In the case of the Aphis gossypii infested plants the results 1 day after treatment (DAT) illustrate the synergistic effect of piperonyl butoxide. The Myzus persicae infested plants were counted through 6 DAT. The 6 DAT on M. persicae also illustrates synergism of compound 1 by piperonyl butoxide.

Percent mortality of Myzus persicae on eggplant 6 DAT foliar application

| | | Piperonyl Butoxide | | |
|---|---|---|---|---|
| | 0 g/ha | 10 g/ha | 20 g/ha | 40 g/ha |
| Compound 1  0 | — | 35 | 0 | 0 |
| 50 g/ha | 30 | 81 | 84 | 95 |
| 12.5 g/ha | 0 | 33 | 79 | 86 |
| 3.13 g/ha | 0 | 0 | 21 | 70 |

Percent mortality of Aphis gossypii on cotton 1 DAT foliar application

| | | Piperonyl Butoxide | | |
|---|---|---|---|---|
| | 0 g/ha | 10 g/ha | 20 g/ha | 40 g/ha |
| Compound 1  0 | — | 23 | 0 | 24 |
| 50 g/ha | 40 | 76 | 91 | 95 |
| 12.5 g/ha | 5 | 57 | 56 | 89 |
| 3.13 g/ha | 0 | 0 | 38 | 80 |

Percent mortality of Aphis gossypii on cucumber 1 DAT foliar application

|  |  | Piperonyl Butoxide | | | |
| --- | --- | --- | --- | --- | --- |
|  |  | 0 g/ha | 10 g/ha | 20 g/ha | 40 g/ha |
| Compound 1 | 0 | — | 23 | 0 | 19 |
|  | 50 g/ha | 80 | 52 | 96 | 91 |
|  | 12.5 g/ha | 34 | 84 | 95 | 82 |
|  | 3.13 g/ha | 0 | 43 | 49 | 69 |

The compounds of the invention may also be used in controlling pests found in non-agricultural domains.

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Orithodorus moubata*) and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,); Diptera (e.g. Aedes spp., Anopheles spp., Dermatobia spp., Haematobia spp., Musca spp., Hippoboscidae spp., Hypoderma spp., Gasterophilus spp., Simulium spp); Stomoxys spp., Hemiptera (e.g. Triatoma spp); Phthirapter (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastro-intestinal tract caused by parasitic nematode worms, for example members of the family Trichostrongyglidae, *Nippostrongylus brasiliensis, Trichinella spiralis, Haemonchus contortus, Trichostrongylus colubriformis, Nematodirus batus, Ostertagis circumcincta, Trichostrongylus axei*, Cooperia spp. and *Hymenolepis nana*; in the control and treatment of protozoal diseases caused by, for example, Eimeria spp. e.g. Eimeria tenella, *Eimeria acervulina, Eimeria brunetti, Eimeria maxima* and *Eimeria necatrix, Trypanosomsa cruzi*, Leishmania spp., Plasmodium spp., Babesis spp., Trichomonadidae spp., Histomonas spp., Giardia spp., Toxoplasma spp., *Entamoeba histolytica* and Theileria spp.

Furthermore the compounds of the invention may be useful for coccidiosis, a disease caused by infections from protozoan parasites of the genus Eimeria.

The compounds are also useful for controlling pests which pose a problem to human health for example mosquitoes (e.g. *Culex quinquefasciatus*) and blackfly (Simulium spp., e.g. *Simulium chutteri* and *S. mcmahoni*). They can be used to control pests found in man-made structures, in particular termites, and provide a good repellency activity against such pests, as well as having a good mammalian toxicity profile, which offers advantages in terms of worker exposure when applying the pesticide to such structures.

They may also be applied against aquatic pests such as motile salmon sea lice (*Lepeophtheirus salmonis*). An advantage of the compounds of the invention is their ability to control such aquatic pests in the presence of non-target organisms, or NTO's. NTO's are chitin-bearing (beneficial) creatures that share the aquatic environment with the pests that it is desirable to control with the compounds of the invention. Examples of NTO's include mayflies, stoneflies, caddisflies (which are important fish foods); sideswimmers, fresh-water shrimp, and crawfish (all crustaceans important to keep the water clean of floating organic debris).

In addition, the control of pests such as grasshoppers (Melanoplus spp., e.g. *Melanoplus sanguinipes*) and locusts (Locustana spp., e.g. *Locustana pardalina*) can be accomplished using the compounds of the invention, either alone or in combination with other materials, e.g. a synergist such as piperonyl butoxide.

The compounds of the invention possess a repellency activity against a number of pests, including rice bug (stinkbug, Nezara spp.), wireworm (Agriotes spp.), cockroaches (Blateila spp. and Periplaneta spp.), whitefly (Bemisia spp.) and termites (Reticulotermes spp.). This type of activity can be useful in many different areas, for example in repelling mosquitoes and ticks and various other biting insects such as those listed above through topical application to skin or clothing.

The low toxicity of the compounds of the invention also offers advantages in a number of other areas including but not limited to the following:

the treatment of pests found in stored grains, for example *Tribolium castaneum, Tribolium confusum, Sitotroga cereaololla, Snagasta kuhniella*, and *Tenebrio molitor*, mothproofing through sprays or incorporation into fibers or application in dry-cleaning agents;

trunk application to trees to prevent upward migration of gypsy moth larvae, and incorporation into greenhouse planting media to reduce fungus gnat, sowbugs, slugs and other soil and plant infestations.

It has also been found that especially useful compositions for animal treatments are mixtures of the compounds of formula (I) with insect growth regulators (IGRs). A particularly preferred mixture is the combination of a compound of formula (I) with lufenuron, {N-[[[2,5-dichloro-4-(1,1,2,3,3, 3-hexafluoropropoxy)phenyl]amino]-carbonyl]-2,6-difluorobenzamide}. Similar mixtures are described in WO95/33380 as being synergistic for agrochemical uses. The mixtures of the invention are most valuable by their long term effect as well as by their good margin of safety for veterinary applications. They are also most useful because of their combined activity on both ticks and fleas, especially those of pets, such as dogs or cats. In particular the compounds of the present invention have a good initial activity against fleas which reduces with time, whereas lufenuron has low activity against fleas after its initial application to the pet, but has greater efficacy some time after application. The combination therefore affords excellent control of fleas over a prolonged period. Furthermore, while lufenuron gives generally rather weak control of ticks, the compounds of the invention give a good level of control over a prolonged period of time after application. The combination of the compounds of the present invention with IGRs, especially lufenuron, therefore surprisingly provides a novel solution to the problem of flea and tick control. Another advantage of such mixtures is that they are well adapted to oral administration. A further advantage is that these combinations provide a prolonged period of control and broad spectrum activity. The appropriate doses are generally from 5 to 50 mg/kg, preferably 10 to 30 mg/kg for the compound of formula (I), "mg/kg" in this instance indicating the milligrams of compound of formula (I) per kilogram of body weight of animal. The amount of IGR partner present in the mixture will vary according to the efficacy of the IGR and the precise conditions of use. One administration per week and preferably one administration per month or more provide generally good efficacy.

The following non-limiting examples further illustrate the invention. In the description that follows, 'DAT' means days after treatment; 'WAT' means Weeks after Treatment; 'HPT' means hours after exposure; 'DPT' means days after exposure; 'ppm' means parts per million; 'a.i.' means active ingredient; 'Dboard' means plywood.

EXAMPLE B1

Experiments were conducted in South Africa in gutters that flowed water over black fly (*Simulium chutteri*) resting sites, and the test compound was applied with a pipettor. Black flies screen out particles so efficiently that they capture essentially 100% of the material flowing through the test channel. The results were as follows:

| Compound No. | 0.05 ppm/10 minutes | 0.1 ppm/10 minutes |
|---|---|---|
| 1 | 40–90% mortality | 70–97% mortality |
| 5 | 0% mortality | 0% mortality |

EXAMPLE B2

The following tests illustrate the activity of compounds of the invention against Horn fly, *Haematobia irritans*. Solutions were applied as a pour-on to cattle and evaluated for the presence or absence of horn fly, expressed as per cent efficacy in keeping the animals fly-free. The compounds of the invention were applied as 1% (10 mg/ml) solutions with an average of 29.5 ml per animal., giving a dosage of about 1 mg a.i. per kg bodyweight of animal. The results were as follows:

|  | 1HPT | 6HPT | 4HPT | 48HPT | 7DPT | 14DPT |
|---|---|---|---|---|---|---|
| Cpd 1 | 98 | 100 | 100 | 99.6 | 100 | 100 |
| Cpd 5 | 96 | 100 | 100 | 99.8 | 100 | 99.2 |

|  | 21DPT | 28DPT | 35DPT | 42DPT | 49DPT |
|---|---|---|---|---|---|
| Cpd 1 | 84 | 81 | 78 | 56 | 40 |
| Cpd 5 | 95 | 93 | 86 | 82 | 89 |

EXAMPLE B3

The following experiment illustrates the activity of compound 1 of the invention against brown dog ticks (*Rhipicephalus sanguineus*). Dogs were given an oral dose of compound in corn oil:DMSO (1:1) at 10 mg/kg body weight, and assessed for the percentage mortality of fleas and ticks (which had dropped off the dog's body) at 1, 9, 16, 23, 30, and 37 days following treatment (DPT).

|  | 1DPT | 9DPT | 16DPT | 23DPT |
|---|---|---|---|---|
| Compound 1 | 100 | 100 | 73 | 68 |

At day 23, the ticks attached to dogs in the treatment were moribund or dead.

EXAMPLE B4

The following experiments were conducted in South Africa and illustrate the activity of the compounds of the invention against brown locusts (*Locustana pardalina*).

A solution of compound 1 (formulated as an emulsifiable concentrate as in Example 3A above) in water was applied by foliar application at a spray volume of 100 ml/ha to fodder sorghum at an application rate equivalent to 10 g/ha active ingredient. One day after application of the active ingredient, field-collected adults locusts were placed on the fodder sorghum. The percentage mortality was assessed in comparison with an untreated control 2 and 3 days after treatment (DAT).

At 2 DAT, about 80% mortality was observed. At 3 DAT, greater than 95% mortality was observed.

EXAMPLE B5

A simulated shampoo treatment was undertaken for compounds of the invention, in which solutions were made up in water and adult head lice (*Pediculus humanus*) were exposed to the solutions for 10 minutes. Mortality was recorded at 24 hours.

Mortality of Pediculus lice exposed to simulated shampoo

|  | rate (ppm) | 24 hour mortality |
|---|---|---|
| water control | — | 4.0 |
| Compound 1 | 2,500 | 58.7 |
|  | 625 | 24.0 |
|  | 156 | 4.1 |

EXAMPLE B6

The following trial was conducted to determine the efficacy of the compounds of the invention against House fly, (*Musca domestica*) found in bovine/poultry manure. Compounds of the invention were applied as a pour-on material to manure and the Table below indicates the degree of control of adult house fly, expressed as per cent control of fly larvae or pupae in manure that failed to eclose to adults.

|  | rate (ppm) | poultry manure | bovine manure |
|---|---|---|---|
| Compound 1 | 1000 | 100 | 100 |
|  | 500 | 100 | 100 |
|  | 250 | 100 | 100 |
|  | 125 | 100 | 99.5 |
|  | 25 | 99.4 | 85.7 |
| Compound 5 | 1000 | 100 | 100 |
|  | 500 | 100 | 100 |
|  | 250 | 100 | 100 |
|  | 125 | 100 | 100 |
|  | 25 | 99.4 | 72.5 |

EXAMPLE B7

Second instar larvae of the Southern House Mosquito (*Culex quinquefasciatus*) were assayed in beakers of water treated with technical compound. LC50's, 4 days following treatment, were determined for Compound 1 as 31.0 parts per billion (ppb). Compound 5 did not cause mortality at the rates tested.

EXAMPLE B8

The following experiment illustrates the activity of compounds of the invention against German cockroach *Blattella germanica*, and the ability of piperonyl butoxide (PBO) to synergize these compounds. Plywood was treated with a spray solution of compound and allowed to age either 1 day or 28 days before exposing cockroaches to the plywood for 2 hours. Mortality of the cockroaches was assessed 72 hours after their exposure to the treated plywood and shown as a percentage mortality. The application rate of the compounds is expressed as an amount of active ingredient in mg/m$^2$.

|         | rate       | 1 Dboards | 28 Dboards |
|---------|------------|-----------|------------|
| Cpd 1   | 400        | 26        | 48         |
|         | 200        | 0         | 8          |
|         | 100        | 6         | 8          |
| Cpd 1 + PBO | 400 + 1200 | 68    | 70         |
|         | 200 + 600  | 44        | 6          |
|         | 100 + 300  | 20        | 24         |
| Cpd 5   | 400        | 100       | 96         |
|         | 200        | 64        | 100        |
|         | 100        | 20        | 18         |
| Cpd 5 + PBO | 400 + 1200 | 82    | 84         |
|         | 200 + 600  | 86        | 60         |
|         | 100 + 300  | 4         | 8          |

EXAMPLE B9

In-vitro screening of Compound 1 was carried out on the motile stages of Salmon Sea Lice, (*Lepeophtheirus salmonis*). Compound 1 was dissolved in propylene glycol and diluted in sea water to give doses of 0.001, 0.01, 0.10, 1.0, 10.0 mg/l. Two replicates of twenty lice each were maintained in the treatments for seventy-two hours. Treatments were compared to sea water controls, and to a DMF solution 1 hour and 1, 2 and 3 DAT. The percentage survival of *L salmonis* are given in the Table below:

| Concentration | Time after exposure | | | |
|---|---|---|---|---|
| Cpd 1 (mg/l) | 1 Hour | 1 DAT | 2 DAT | 3 DAT |
| 0     | 100 | 90.5 | 92.5 | 85.0 |
| 0.001 | 100 | 95.0 | 97.5 | 87.5 |
| 0.01  | 100 | 17.5 | 0    | 0    |
| 0.1   | 100 | 0    | 0    | 0    |
| 1.0   | 0   | 0    | 0    | 0    |
| 10.0  | 0   | 0    | 0    | 0    |

These results clearly illustrate the ability of the compounds of the invention to control salmon lice, for example as an oral treatment, particularly in view of their good aquatic toxicological profile.

EXAMPLE B10

The following trial was done on stinging wasp (Polistes spp) nests. Polistes spp. are the wasps that build a paper cone under the eaves of buildings, and in protected places. Solutions of compound 1 were made up as emulsifiable concentrate formulations, and sprayed with a pump-up sprayer directly on the nest for 3–5 seconds. Coverage extended to the whole nest wherever possible, to make sure all wasps on the nest were wetted. Foragers that were away from the nest were exposed only if they returned to the nest. Nests with 12 or more individuals were selected for treatment, and the beginning and end numbers counted. The results (expressed as a percentage control of Polistes spp) were as follows:

|              | 1 DAT | 3 DAT | 7 DAT |
|--------------|-------|-------|-------|
| Cpd 1 @ 0.25% | 88.9 | 91.7  | 97.2  |
| Cpd 1 @ 1.0%  | 100  | 100   | 98.2  |

EXAMPLE B11

A bioassay was run on Eastern subterranean termite (*Reticulotermes flavipes*) as a treated soil, no-choice test with the termites confined to treated soil. Two milliliters of solution were applied to each treatment cup, acetone allowed to dry off, and termites introduced. Test was read at one week and again at two weeks to determine mortality, which is expressed as ppm of the treatment solution. This test was rerun to verify the results. The values expressed are the average of the two trials.

|            | LC50 ppm 1 WAT | LC50 ppm 2 WAT |
|------------|----------------|----------------|
| Compound 5 | 3.6            | 0.39           |
| Compound 1 | 2.6            | 0.38           |

Also in a termite bait test, Compound 1 was placed into bait blocks and offered to 300 worker termites. The test had one block treated and one block untreated, with the baits being attached to the main termite colony by neoprene tubing, so that termites had to seek out the bait. The termites were either killed at the bait site or were able to move on from the bait, leaving a pheromone trail for following foragers. Initial death took place at the bait site, causing following termites to disregard the bait further. The results are indicated below (Note that the figure in parenthesis is the ratio of the percentage bait consumed:percentage consumed in the untreated block):

|       | 10 ppm    | 1 ppm     | 0.1 ppm  | 0.01 ppm |
|-------|-----------|-----------|----------|----------|
| Cpd 1 | 8         | 21        | 26       | 39       |
|       | (23:167)  | (53:141)  | (77:98)  | (61:77)  |

Compositions

Solid or liquid compositions for application topically to animals, timber, stored products or household goods usually contain from about 0.00005% to about 90%, more particularly from about 0.001% to about 10%, by weight of one or more compounds of general formula (I). For administration to animals orally or parenterally, including percutaneously, the solid or liquid compositions normally contain from about 0.1% to about 90% by weight of one or more compounds of general formula (I). Medicated feedstuffs normally contain from about 0.001% to about 3% by weight of one or more compounds of general formula (I). Concentrates or supplements for mixing with feedstuffs normally contain from about 5% to about 90%, preferably from about 5% to about 50%, by weight of one or more compounds of general formula(I). Mineral salt licks normally contain from about 0.1% to about 10% by weight of one or more compounds of general formula (I).

Dusts or liquid compositions for application to livestock, persons, goods, premises or outdoor areas may contain from about 0.0001% to about 15%, more especially from about 0.005% to about 2.0%, by weight, of one or more compounds of general formula (I). Suitable concentrations in treated waters are between about 0.0001 ppm and about 20 ppm, more particularly from about 0.001 ppm to about 5.0 ppm of one or more compounds of general formula (I) and may be used therapeutically in fish farming with appropriate exposure times. Edible baits may contain from about 0.01% to about 5%, preferably from about 0.01% to about 1.0%, by weight, of one or more compounds of general formula (I).

When administered to vertebrates parenterally, orally or by percutaneous or other means, the dosage of compounds of general formula (I) will depend upon the species, age and health of the vertebrate, and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A synergistic pesticidal composition comprising:
   (a) a pesticidally effective amount of a compound having the formula:

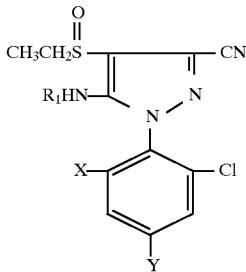

wherein X is chlorine or bromine, Y is trifluoromethyl or trifluoromethoxy and $R_1$ is hydrogen, methyl or ethyl; and
   (b) a synergistic amount of piperonyl butoxide.

2. A composition according to claim 1 in which, in the compound of formula (I), X is chlorine and Y is trifluoromethyl.

3. A composition according to claim 1 in which, in the compound of formula (I), $R_1$ is hydrogen or methyl.

4. A composition according to claim 2 in which, in the compound of formula (I), $R_1$ is hydrogen or methyl.

5. The composition according to claim 1 in which the compound of formula (I) is:
   5-amino-3-cyano-1-(2,6-dichloro-4-trifluoromethylphenyl)-4-ethylsulfinylpyrazole;
   5-amino-3-cyano-1-(2,6-dichloro-4-trifluoromethoxyphenyl)-4-ethylsulfinylpyrazole;
   5-amino-1-(2-bromo-6-chloro-4-trifluoromethylphenyl)-4-ethylsulfinylpyrazole;
   5-amino-1-(2-bromo-6-chloro-4-trifluoromethoxyphenyl)-4-ethylsulfinylpyrazole;
   3-cyano-1-(2,6-dichloro-4-trifluoromethylphenyl)-4-ethylsulfinyl-5-methylaminopyrazole;
   3-cyano-1-(2,6-dichloro-4-trifluoromethylphenyl)-4-ethylsulfinyl-5-ethylaminopyrazole; or
   1-(2-bromo-6-chloro-4-trifluoromethoxyphenyl)-4-ethylsulfinyl-5-ethylaminopyrazole.

6. The composition according to claim 1 in which the compound of formula (I) is 5-amino-3-cyano-1-(2,6-dichloro-4-trifluoromethylphenyl)-4-ethylsulfinylpyrazole.

7. The composition according to claim 1 in which the compound of formula (I) is 3-cyano-1-(2,6-dichloro-4-trifluoromethylphenyl)-4-ethylsulfinyl-5-methylaminopyrazole.

8. A synergistic pesticidal composition comprising:
   (a) a pesticidally effective amount of a compound having the formula:

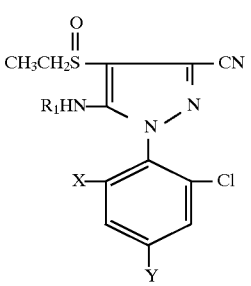

wherein X is chlorine or bromine, Y is trifluoromethyl or trifluoromethoxy and $R_1$ is hydrogen, methyl or ethyl;
   (b) a synergistic amount of piperonyl butoxide; and
   (c) at least one member selected from the group consisting of a pesticidally acceptable carrier and a pesticidally acceptable surface-active agent.

9. A composition according to claim 8 in which, in the compound of formula (I), X is chlorine and Y is trifluoromethyl.

10. A composition according to claim 8 in which, in the compound of formula (I), $R_1$ is hydrogen or methyl.

11. A composition according to claim 9 in which, in the compound of formula (I), $R_1$ is hydrogen or methyl.

12. The composition according to claim 8 in which the compound of formula (I) is:
    5-amino-3-cyano-1-(2,6-dichloro-4-trifluoromethylphenyl)-4-ethylsulfinylpyrazole;
    5-amino-3-cyano-1-(2,6-dichloro-4-trifluoromethoxyphenyl)-4-ethylsulfinylpyrazole;
    5-amino-1-(2-bromo-6-chloro-4-trifluoromethylphenyl)-4-ethylsulfinylpyrazole;
    5-amino-1-(2-bromo-6-chloro-4-trifluoromethoxyphenyl)-4-ethylsulfinylpyrazole;
    3-cyano-1-(2,6-dichloro-4-trifluoromethylphenyl)-4-ethylsulfinyl-5-methylaminopyrazole;
    3-cyano-1-(2,6-dichloro-4-trifluoromethylphenyl)-4-ethylsulfinyl-5-ethylaminopyrazole; or
    1-(2-bromo-6-chloro-4-trifluoromethoxyphenyl)-4-ethylsulfinyl-5-ethylaminopyrazole.

13. The composition according to claim 12 in which the compound of formula (I) is 5-amino-3-cyano-1-(2,6-dichloro-4-trifluoromethylphenyl)-4-ethylsulfinylpyrazole.

14. The composition according to claim 12 in which the compound of formula (I) is 3-cyano-1-(2,6-dichloro-4-trifluoromethylphenyl)-4-ethylsulfinyl-5-methylaminopyrazole.

15. A method for controlling the growth of pests at a locus which comprises applying to said locus a pesticidally effective amount of a synergistic pesticidal composition comprising:
    (a) a pesticidally effective amount of a compound having the formula:

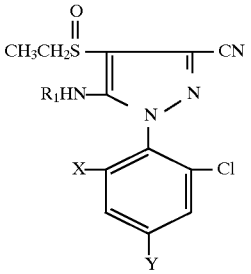

wherein X is chlorine or bromine, Y is trifluoromethyl or trifluoromethoxy and $R_1$ is hydrogen, methyl or ethyl; and
    (b) a synergistic amount of piperonyl butoxide.

16. A method according to claim 15 in which the dose rate of the compound of formula (I) is from about 5 to about 1000 g/ha and the dose rate of piperonyl butoxide is from about 10 to about 200 g/ha.

17. A method according to claim 16 in which the dose rate of piperonyl butoxide is from about 20 to about 100 g/ha.

18. A method according to claim 17 in which the dose rate of piperonyl butoxide is about 40 g/ha.

19. A method according to claim 15 in which the locus is an area used, or to be used, for the growing of crops.

20. A method according to claim 15 in which the locus is other than an agricultural area.

21. A method according to claim 15 in which, in the compound of formula (I), X is chlorine and Y is trifluoromethyl.

22. A method according to claim 15 in which, in the compound of formula (I), $R_1$ is hydrogen or methyl.

23. A method according to claim 21 in which, in the compound of formula (I), $R_1$ is hydrogen or methyl.

24. A method according to claim 15 in which the compound of formula (I) is:

5-amino-3-cyano-1-(2,6-dichloro-4-trifluoromethylphenyl)-4-ethylsulfinylpyrazole;

5-amino-3-cyano-1-(2,6-dichloro-4-trifluoromethoxyphenyl)-4-ethylsulfinylpyrazole;

5-amino-1-(2-bromo-6-chloro-4-trifluoromethylphenyl)-4-ethylsulfinylpyrazole;

5-amino-1-(2-bromo-6-chloro-4-trifluoromethoxyphenyl)-4-ethylsulfinylpyrazole;

3-cyano-1-(2,6-dichloro-4-trifluoromethylphenyl)-4-ethylsulfinyl-5-methylaminopyrazole;

3-cyano-1-(2,6-dichloro-4-trifluoromethylphenyl)-4-ethylsulfinyl-5-ethylaminopyrazole; or 1-(2-bromo-6-chloro-4-trifluoromethoxyphenyl)-4-ethylsulfinyl-5-ethylaminopyrazole.

25. The method according to claim 15 in which the compound of formula (I) is 5-amino-3-cyano-1-(2,6-dichloro-4-trifluoromethylphenyl)-4-ethylsulfinylpyrazole.

26. The method according to claim 25 in which the dose rate of the compound of formula (I) is from about 5 to about 1000 g/ha and the dose rate of piperonyl butoxide is from about 10 to about 200 g/ha.

27. The method according to claim 26 in which the dose rate of piperonyl butoxide is from about 20 to about 100 g/ha.

28. The method according to claim 27 in which the dose rate of piperonyl butoxide is about 40 g/ha.

29. The method according to claim 25 in which the dose rate of the compound of formula (I) is from about 3.13 to about 50 g/ha and the dose rate of piperonyl butoxide is from about 10 to about 40 g/ha.

* * * * *